United States Patent [19]
Etzkorn et al.

[11] Patent Number: 6,080,838
[45] Date of Patent: Jun. 27, 2000

[54] PEPTIDOMIMETIC OF HELIX-TURN-HELIX OR GAMMA-TURN

[75] Inventors: Felicia A. Etzkorn; Jeremy M. Travins, both of Charlottesville, Va.

[73] Assignee: University of Virginia Patent Foundation, Charlottesville, Va.

[21] Appl. No.: 08/978,023

[22] Filed: Nov. 25, 1997

[51] Int. Cl.[7] ...................................................... A61K 38/00
[52] U.S. Cl. ......................... 530/324; 530/317; 530/333; 514/12
[58] Field of Search .................................... 530/350, 324, 530/317; 514/12, 2, 11, 9

[56] References Cited

PUBLICATIONS

Travins, et al., "Design and Enantioselective Synthesis of a Peptidomimetic of the Turn in the Helix–Turn–Helix DNA–Binding Protein Motif" J. Org. Chem., 1997, 62, 8387–93, 1997.

*Primary Examiner*—Cecilia J. Tsang
*Assistant Examiner*—Fabian A. Jameison
*Attorney, Agent, or Firm*—Oblon, Spivak, McClelland, Maier & Neustadt, P.C.

[57] ABSTRACT

A peptidomimetic of the turn in the helix-turn-helix (HTH) motif of DNA-binding proteins was designed and synthesized. Conformational constraint was achieved by an unusual linking of two amino acids with a side-chain carbon—carbon bond. A phenyl ring provides the potential for new hydrophobic contacts with the hydrophobic core of the HTH motif. In the mimic, the peptide backbone and the central residue were retained in native form within a 12-membered cyclic tripeptide. The target compound 1b was synthesized by two sequential Horner-Wittig couplings followed by enantioselective hydrogenation with Rh(MeDuPHOS) in 8 steps and 35% overall yield. The stereochemical outcome of the key hydrogenation was determined by aromatic ring oxidation with $RuO_2/NaIO_4$ to give two equivalents of Boc-Asp-OMe.

5 Claims, 4 Drawing Sheets

2a Native Cro Peptide: Ac-TQTELATKAGVKQQSIQLEAGV-NH$_2$, SEQ ID No.= 1
2b Cro Peptidomimetic: Ac-TQTELATK--1--KQQSIQLIEAGV-NH$_2$, SEQ ID No. = 2

2a Native Cro Peptide: Ac-TQTELATKAGVKQQSIQLEAGV-NH$_2$, SEQ ID No.= 1
2b Cro Peptidomimetic: Ac-TQTELATK--1--KQQSIQLIEAGV-NH$_2$, SEQ ID No. = 2

1a,b

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Thr Gln Thr Glu Leu Ala Thr Lys Ala Gly Val Lys Gln Gln Ser Ile
   1           5                  10              15

Gln Leu Ile Glu Ala Gly Val
           20

(2) INFORMATION FOR SEQ ID NO:2:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Thr Gln Thr Glu Leu Ala Thr Lys Xaa Lys Gln Gln Ser Ile Gln Leu
   1           5                  10              15

Ile Glu Ala Gly Val
           20

PEPTIDOMIMETIC OF HELIX-TURN-HELIX OR GAMMA-TURN

BACKGROUND OF THE INVENTION

Field of the Invention

This invention pertains to DNA binding protein or peptide mimics and more specifically to peptide-based mimics which present two peptide helices held in an unusually tight turn of the DNA-binding conformation. Additionally, this invention pertains to the synthetic construct prepared to hold the two peptide helices in tight arrangement so as to mimic peptide DNA binding conformation. A cyclic structure provides the constraints necessary, and hydrogen bonding essential, to mimic the helix-turn-helix structure of DNA binding proteins. This permits the synthesis of small but stable helix-turn-helix peptides.

BACKGROUND OF THE PRIOR ART

DNA binding by proteins and peptide structures remains one of the most intriguing and least understood sub-cellular processes essential for biological functioning. Antibacterial agents, transcription and transcription inhibition, and a host of similarly basic biological events are mediated, to some degree, by protein binding of DNA. Yet, DNA recognition, release and triggering events are, at best, poorly understood or predicted. Identification of peptides which effectively and functionally recognize DNA remains a largely trial and error process.

The study and elucidation of peptide binding of DNA is hampered to some degree because of the current need to study whole protein units. Smaller peptides, while easier to manage and study, deprived of the conformational stability provided by the quaternary structure mechanisms of the whole protein to which they correspond, may lack the structural stability necessary to achieve DNA binding. Binding events must be, at a minimum, an issue of matching molecular topography. In particular, it is especially difficult to maintain the unusually tight turn of the helix-turn-helix peptide motif predisposed to peptide binding. The use of whole proteins, on the other hand, tends to obscure that which is sought to be shown, and often introduces other factors difficult to control. Ultimately, the identification of synthetic DNA-binding peptides will permit treatment of a variety of conditions mediated by this event and provide a powerful new class of pharmaceuticals.

Accordingly, it remains a goal of those of skill in the art to provide a synthetic moiety which will hold two protein helices in the proper spatial alignment to facilitate peptide binding of DNA, so that this phenomenon may be further studied.

Another object of the art is to provide a moiety by which synthetic short chain DNA-binding peptides or dipeptides which exhibit selective DNA-binding properties may be prepared. These and other objects are achieved by the invention set forth below.

SUMMARY OF THE INVNTION

The "turn" of a helix-turn-helix DNA-binding peptide structure is mimicked by the cyclic moiety

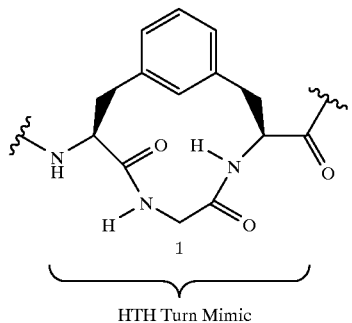

HTH Turn Mimic

This can be linked, through amide linkage, with two peptides which exhibit helices that can recognize DNA binding. Although this invention is described with reference to a particular linked triipeptide mimetic, any two suitable peptide helices may be paired through the synthetic turn moiety of the invention, to provide a potential binding peptide.

The helix-turn-helix (HTH) structural motif is found in DNA-binding proteins. From prokaryotic repressors of transcription to eukaryotic homeodomain transcription activators, the motif is well-suited to bind DNA. Of the two helices, one binds DNA directly in the major groove and is stabilized by a second backing helix at right angles to the first, FIG. 1. Between these two helices is a hydrophobic core that serves to stabilize the tertiary interactions between the two helices. The helices are connected via a tight turn that resembles the seven-member hydrogen-bonded ring of the classical γ-turn. The turn of the helix-turn-helix (HTH) motif is distinct from the more common β-turn. The HTH-turn is tighter, containing only three amino acid residues, while β-turns have four residues.[1] The HTH turn lacks the hydrogen bond of the γ-turn, and consequently the backbone (and T angles differ from the classical γ-turn angles.

To study the molecular recognition process between proteins and DNA, we wish to synthesize peptidomimetics corresponding to the small DNA-binding HTH motif. Since short peptides are usually not conformationally stable in the absence of the constraints from the whole protein, we designed a small peptidomimetic turn, 1, to stabilize the HTH motif in small peptides, FIG. 1. The mimic was designed to stabilize the tertiary structure of the HTH motif found in DNA-binding proteins such as the bacteriophage 434 Cro protein[2,3] or repressor protein or eukaryotic homeodomain proteins, such as Oct-1, that are key developmental transcription factors.[4,5]

Two principles were used to design the turn peptidomimetic: 1) conformational constraint via side-chain covalent bonds, and 2) introduction of additional hydrophobic contacts in the core of the HTH motif.[6] A wide variety of covalent bonds, from disulfides and amides to carbon—carbon bonds could constrain the conformation, but the new bonds must not interfere with the existing sterics or electronics of the motif. Mullen and Barlett designed a template for the outside of the turn region of the HTH motif.[7] Our template is designed to be tucked into the hydrophobic core of the HTH motif, inside the turn, so that the native-like backbone is retained. We chose to make a hydrocarbon-bridged turn mimic because the carbon—carbon bond would be stable and would suite the steric constraints in the core of the tight turn. Although the mimic is rigidified relative to the natural turn motif, the 12-membered ring is somewhat flexible. This flexibility is desirable when the conformation of the natural motif cannot be matched exactly or is bounded by the uncertainty of the X-ray or NMR structure that the mimic was modeled upon. Hydrophobic contacts between side-chains within the two helices and the turn mimic are expected to stabilize the hydrophobic core of this peptide fragment taken from the Cro protein. The phenyl ring thus satisfies the second criterion of introducing hydrophobic contacts, as shown in FIG. 2. Hydrophobic contacts between peptide side-chains and β-turn mimics have been used successfully to stabilize β-sheet peptides,[6,8–10] and a β-sheet/α-helix tertiary motif.[11] The central amino acid residue of the HTH turn mimic can be readily varied in cassette fashion to accommodate the various hydrophilic side-chains found in different members of the HTH structural family. The molecule was designed in an iterative process of molecular modeling and synthetic considerations.

The synthetic considerations in the design of mimic 1 required construction of a unique α,ω-diaminodicarboxylate with β-carbons from two α-amino acid backbones attached meta- to a single phenyl side-chain. Because of this requirement, each of the four functional groups had to be orthogonally protected. Two stereocenters corresponding to L-amino acid configurations had to be incorporated to retain the designed hydrophobic interactions. Finally, a medium-ring had to be closed either at a carbon—carbon bond or at an amide bond. We chose the amide-bond closure for synthetic simplicity.

Stereoselective amino acid synthesis has been reviewed.[12] The turn mimic is an example of the less common side-chain bridged α,ω-diaminodicarboxylates, of which there are many examples,[13–17] but few that are carbon—carbon linked.[18,19] Synthesis of unnatural amino acids was greatly advanced by the development of stereoselective catalysts for the hydrogenation of didehydroamino acids.[20–22] The C2-symmetric chiral catalyst, Rh((2S,5S-dimethyl)-1,2-bisphospholanobenzene) (MeDUPHOS), cleanly reduces didehydroamino acids to the corresponding L-amino acid in high yield and high enantioselectivity.[23–25] Synthesis of the precursor didehydroamino acids was facilitated by the development of an α-amino acid Horner-Wittig reagent.[26] The Wittig reaction and Horner-Wadsworth-Emmons modifications were reviewed in 1989.[27] We have taken advantage of the powerful enantioselective hydrogenation of didehydroamino acids to synthesize turn mimic 1b. Simultaneous enantioselective hydrogenation of two aminoacrylate centers in a single molecule is a key feature of our synthesis.[28]

DETAILED DESCRIPTION OF THE INVENTION

Reference may be had to FIGS. 1–4 submitted herewith. These Figures are not believed necessary for an understanding of the invention, but are advanced to better facilitate an appreciation of the nature of the invention.

RESULTS AND DISCUSSION

Design of the Mimic

Figure 1:
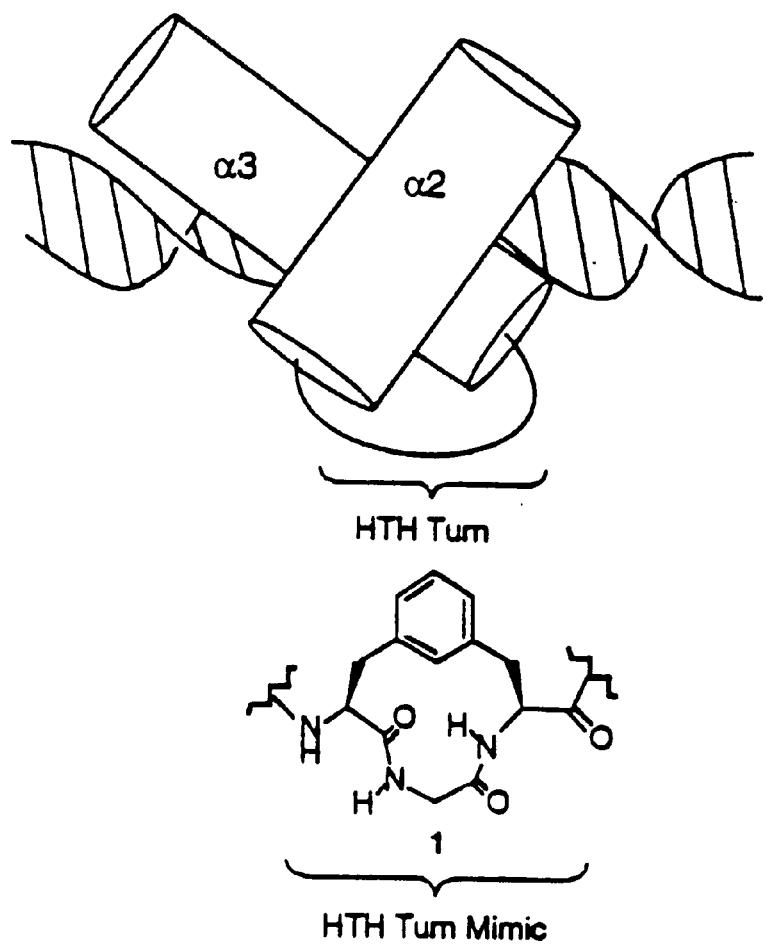
FIG. 1 illustrates the binding of DNA by the helix-turn-helix (HTH) motif. Beneath is the HTH turn mimic 1 used in molecular modeling design work. Sequence of the Cro HTH native peptide 2a and peptide with HTH turn mimic 2b used in modeling is also shown.
Figure 3:
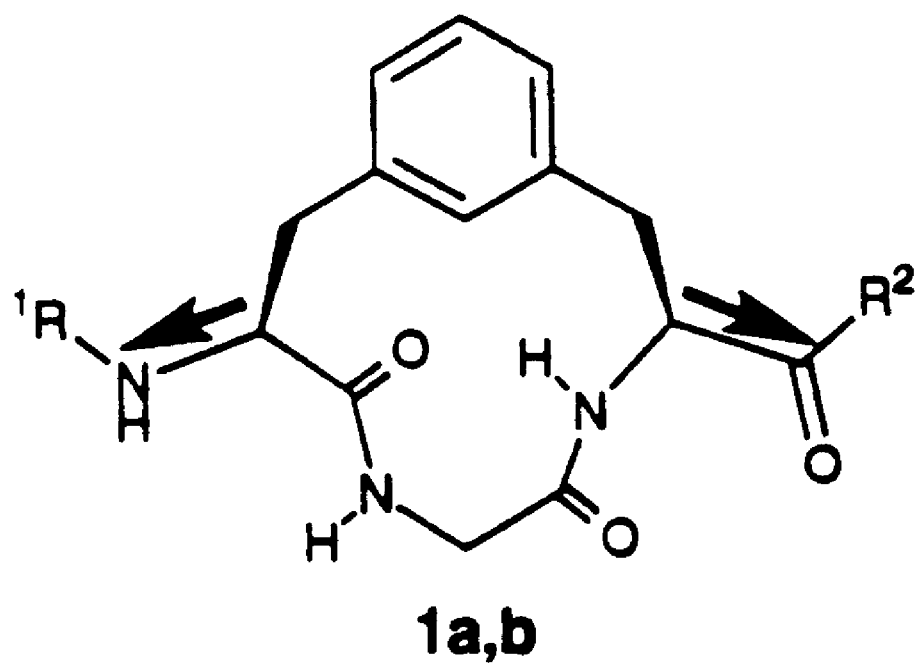
FIG. 3 illustrates the turn mimic 1a. R1=CH3CO—, R2=NHMe. Synthetic target 1b R1=tBuOCO−, R2=OH.

A model of the HTH turn mimic 1a, FIG. 3, was constructed and the global minimum conformation was explored using Macromodel v. 3.5. First, the X-ray crystal structure of the Cro protein bound to OR1 DNA[3] was edited to remove the DNA and most of the protein, leaving a 23 residue HTH peptide, Cro16–38 FIG. 1. Only helical residues were included at the C- and N-termini. The C-terminus was modified to a carboxamide and the N-terminus was acetylated for all modeling. The turn mimic 1a was built by removing all but the β-carbons from the side-chains of Ala21 and Val23 and connecting a phenyl group to the two β-carbons. To search for the global minimum, 1000 starting structures of 1a were generated by the Macromodel Monte Carlo dihedral angle conformational search option and minimized using the Amber force field with water salvation. Of the 129 unique conformations found, 65 minimized with good convergence. The lowest energy conformation, found 15 times, was 6 kJ/mole lower than the next conformer, found 17 times.

Figure 4:
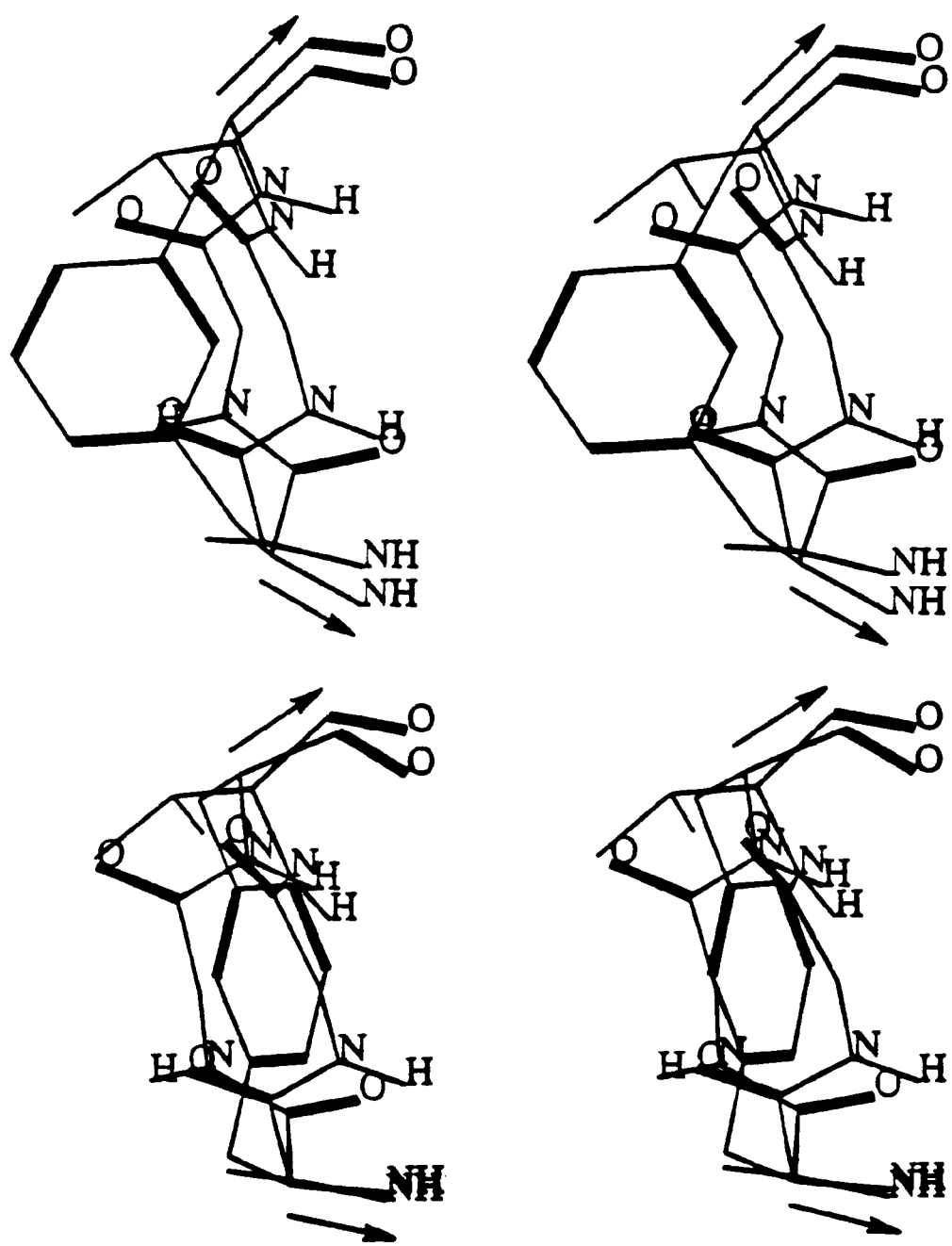
FIG. 4 is a stereodrawing of the superpositon of the backbone vectors of the turn residues of 1a, shown with arrows, with the corresponding vectors of the two lowest energy conformers, rmsd 0.38 Anstrom with the lowest energy conformer (top) and 0.16 with the second lowest (bottom).

The two lowest energy conformers were incorporated into the backbone of the HTH Cro peptide 2a and minimized using MacroModel Amber and water solvation. Superposition of all α-carbons of the resulting HTH peptodomimetics 2b with Cro HTH peptide 2a (lowest energy rmsd 0.80 Å, second lowest 0.71 Å) suggests minimal alteration of the three-dimensional structure of the HTH motif (data not shown). The ΦAla24 and ΨVal26 backbone vectors[29–31] set the direction for the two helices with respect to the ring. FIG. 4 shows the superposition of these vectors in the turn of 1a with the corresponding vectors of the two low energy conformers in 2b, rmsd 0.38 Å with the lowest energy conformer, and 0.16 Å with the second lowest. The two conformers have different orientations of the phenyl ring with respect to the backbone, reflecting the range of conformational flexibility designed into the turn mimic, FIG. 4.

In the lowest energy conformer of the turn mimic, no hydrogen bond was formed between the C=O and NH that normally would form in a γ-turn. Since this hydrogen bond is also absent in the native turn, this implies that the C=O and NH of the mimic will be available for hydrogen bonding to the helices as in the native protein. In the X-ray structure, the extra-turn hydrogen bond to the α2 helix is implied by a distance of 2.01 Å between the Ala21 C=O and the Val26 NH in the turn. The analogous hydrogen bond is also found in the HTH peptidomimic 2b. In the second lowest energy conformer of 1a the γ-turn hydrogen bond is present. The existence of this structure in a nearby minimum indicates that the HTH turn mimic may make a satisfactory γ-turn mimic as well.

Figure 2:
FIG. 2 is a CPK model of the HTH turn mimic minimized in the context of the X-ray structure of Cro peptide 2b. The phenyl ring and three of the helix side-chains involved in hydrophobic interactions are labeled. Ala21 is buried.

Five hydrophobic contacts between the turn mimic and helix sidechains were found in the minimized peptidomimetic 2b, FIG. 2, specifically: 1) Ph1-proS-βH to Leu20-proS-δCH$_3$, 2.1 Å, 2) Ph2H to Ala21-αH, 1.4 Å, 3) Ph2H to Ile31-δCH$_3$, 2.2 Å, 4) Ph3-proR-βH to Ile31-δCH$_3$, 2.3 Å, and 5) Ph3-proR-βH to Ser30-βH, 1.8 Å. Two hydrophobic contacts were found in the turn of the native Cro HTH peptide 2a, 1) Val26-γH to Ile31-δCH$_3$, 2.3 Å, and 2) Ala24-βCH$_3$ to Leu20-proS-δCH$_3$, 3.1 Å. The design of the turn mimic thus incorporates potential hydrophobic stabilization of the HTH motif using the aryl sidechain conformational constraint.

Synthesis

α,ω-Diaminodiacrylate

Despite the apparent simplicity, the synthesis of the aryl turn mimic requires orthogonal protection on four functional groups, two amines and two carboxylic acids. The amino acid synthon, 3, was first reported in a series of protected amino phosphorylacetate esters.[26] Trimethylsilylethyl 2-Boc-2-(dimethoxyphosphoryl)acetate, 5, fits our criteria of ease of synthesis and orthogonal protection. The use of 5, without its synthesis, has been reported.[32] We now report the synthesis and characterization of this key starting material, Scheme 1.

Scheme 1
Synthesis of orthogonally-protected amino acid synthon

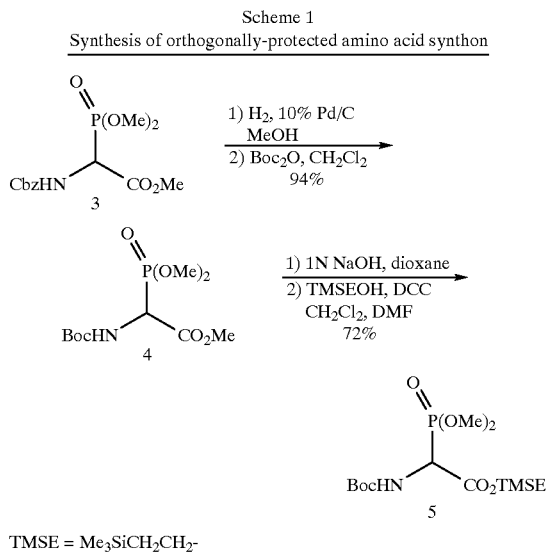

TMSE = Me₃SiCH₂CH₂-

Preparation of the aminoacrylate 6 was achieved in 94% yield by reaction of 10-fold excess of the commercially available benzene-1,3-dialdehyde with phosphonate 3, Scheme 2. Reaction of phosphonate 5 with mono-aldehyde 6 produced orthogonally-protected 7 in 83% yield.[33] Under conditions with tetramethylguanidine as base, we observed predominantly one diastereomer in the ¹H-NMR, presumably Z based on the literature precedence.[28] The one-step synthesis of a meta-substituted phenyl α,ω-diaminodiacrylate has been reported, though not orthogonally protected.[26] Hydrogenation to the et,wdiaminodicarboxylate was not reported.

Scheme 2
Synthesis of α, ω-diaminodiacrylate

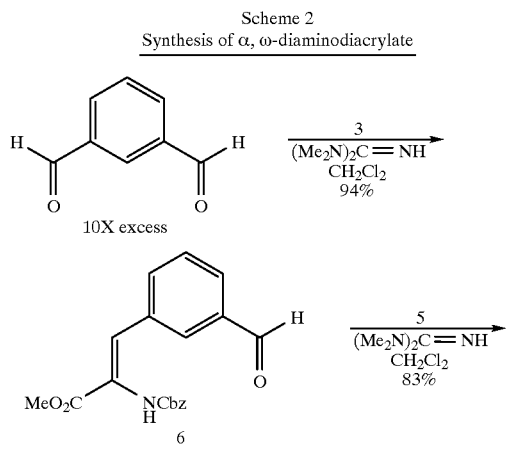

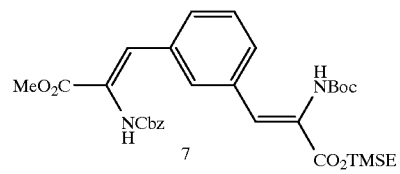

Enantioselective Hydrogenation

Rh(MeDUPHOS)[34] gives excellent enantioselectivity and high yields for both Z and E olefins regardless of amino acid protecting groups.[23] The double enantioselective hydrogenation of 7 produced α,ω-diaminodicarboxylate 8 in excellent yield, Scheme 3. Hydrogenation using Wilkinson's catalyst gave a racemic mixture of diastereomers 8. The aryl singlets were well-resolved in the ¹H-NMR spectra of partially purified diastereomeric mixtures of 8. Integration[35] of the aryl singlet of the hydrogenated product gave a 98:2 diastereomeric ratio. Since the catalyst is known to produce L-amino acid stereochemistry,[23] this indicates that small amounts of S,R- or R,S-isomer were formed in the hydrogenation, with the major product being the S,S-diastereomer, mimicking the natural L,L-stereochemistry of the turn.

Scheme 3
Enantioselective hydrogenation of 7

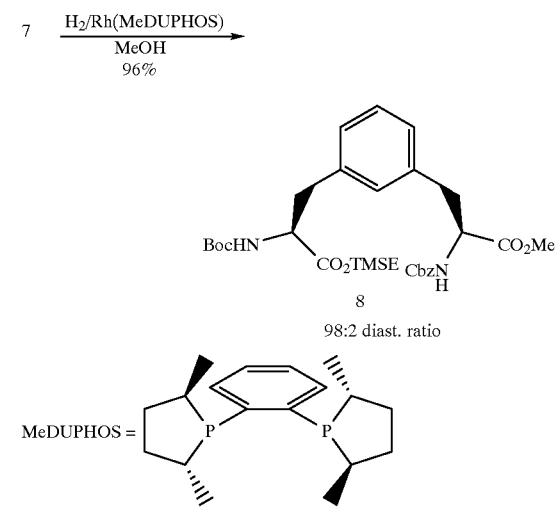

Proof of the S,S-stereochemistry was obtained by chemical degradation of the reduced intermediate 8, Scheme 4. Preparation of a symmetrical derivative followed by oxidative cleavage of the aromatic ring produced Boc-Asp-OMe of known configuration. Boc-protected amines are stable to RuO₄ oxidative conditions.[36] We avoided the presence of Cbz because it is not stable to the reaction conditions.[37] Thus we chose to produce the Boc and methyl ester protected symmetric derivative 11 for oxidative cleavage.

Removal of the trimethylsilylethy (TMSE) ester with fluoride gave acid 9, also the next step in the synthesis, Scheme 4. Under rigorously dry conditions in the desilylation, we observed epimerization. However, deliberate addition of water to the reaction resulted in clean removal of the TMSE ester without epimerization. Esterification with (trirnethylsilyl)diazomethane gave the bis-methyl ester 10. The Cbz amino protecting group was switched to Boc by hydrogenolysis in the presence of di-tert-butyl dicarbonate (Boc₂O) to afford 11. The optical rotation of this intermediate, $[\alpha]_D=+46.3°\pm0.5$, demonstrated that the major product was one of the $C_2$ symmetric stereoisomers (R,R— or S,S—) and not the meso isomer. Oxidation of 11 with $RuO_2$ and an excess of $NaIO_4$ for 12 h produced Boc-Asp-OMe with $[\alpha]_D=17.9°\pm0.5$ (lit. −17.8° and −19°). We have thus synthesized the unusual α,ω-diaminodicarboxylate 8 with the desired S,S-sterochemistry.

Scheme 4
Proof of stereochemistry by chemical degradation to
Boc — Asp — OMe

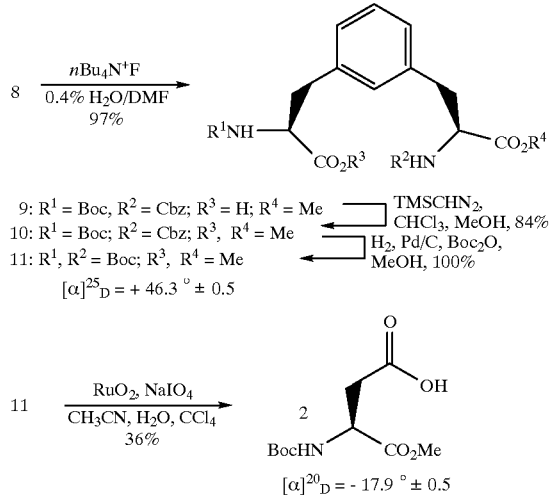

9: R¹ = Boc, R² = Cbz; R³ = H; R⁴ = Me  ⎤ TMSCHN₂,
10: R¹ = Boc; R² = Cbz; R³, R⁴ = Me     ⎦ CHCl₃, MeOH, 84%
11: R¹, R² = Boc; R³, R⁴ = Me           ⎤ H₂, Pd/C, Boc₂O,
                                         ⎦ MeOH, 100%
$[\alpha]^{25}_D = +46.3° \pm 0.5$ 11 →(RuO₂, NaIO₄ / CH₃CN, H₂O, CCl₄ / 36%)→ 2

$[\alpha]^{20}_D = -17.9° \pm 0.5$

Cyclization

Coupling of the tosylate salt of benzyl glycinate with acid 9 proceeded smoothly to give the protected acyclic precursor 12, Scheme 5. Simultaneous hydrogenolysis of the Cbz and Bn protecting groups followed by cyclization with diphenylphosphoryl azide (DPPA) in dilute DMF solution afforded cyclic tripeptide methyl ester 13 in high yield.[40] In anticipation of future incorporation of amino acids beside Gly into the mimic, DPPA was chosen for cyclization because of the low propensity of acyl azides to racemize.[41] This cyclization has also been performed with Ala in the central position in 80% yield.

Scheme 5
Tripeptide formation, cyclization, and deprotection of turn mimic

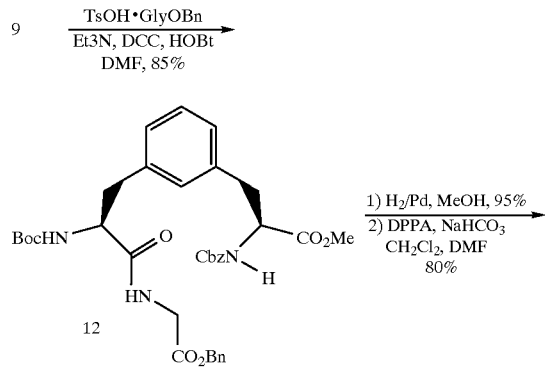

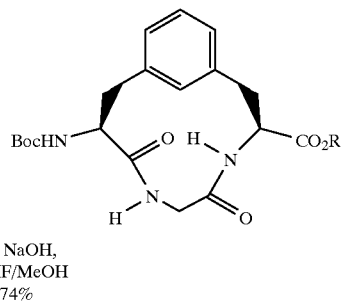

13: R = Me  ⎤ 1N NaOH,
1b: R = H   ⎦ THF/MeOH
             74%

The methyl ester was hydrolyzed with one equivalent 1 N NaOH in THF/MeOH to give 74% yield of the free acid product 1b. This brief, high-yielding synthesis has allowed the preparation of the quantities of 1b necessary for peptide synthesis (825 mg). Peptidomimetic 2b has been synthesized on solid phase using compound 1b.

Conclusion

We have synthesized a mimic of either the HTH-turn or γ-turn that is designed to stabilize the HTH motif by both conformational constraint and hydrophobic interactions. The mimic was synthesized in 8 steps from phosphonates 3 and 5, using two sequential Horner-Wittig reactions followed by simultaneous enantioselective hydrogenation of both aminoacrylates to give the native-like stereochemistry. Macrocyclization of the tripeptide proceeded in 80% yield. Turn mimic 1b was synthesized in eight steps and 35% overall yield.

Experimental

All chemicals were reagent grade and commercially available. Rh(MeDUPHOS) was obtained from Strem Chemicals Inc. Unless otherwise indicated, all reactions were carried out under $N_2$ atmosphere, in flame-dried flasks. THF and $Et_2O$ were distilled from dark blue solutions with K and benzophenone. Benzene, toluene, $CH_2Cl_2$, $CH_3CN$, $Et_3N$, and diisopropylethylamine (DIEA) were distilled from $CaH_2$ under $N_2$ atmosphere. DMF and MeOH were dried with 3 Å molecular sieves. Chromatography was on 32–63 μm silica gel with reagent grade solvents. TLC was performed using aluminum-backed silica gel plates. Melting points are uncorrected. Proton (300 MHZ) and carbon-13 (75 MHZ) NMR spectral data were recorded on a General Electric spectrometer using deuterated solvents at approximately 22° C.

2-(Trimethylsilyl)ethyl 2-(tert-butoxycarbonylamino)-2-(dimethoxyphosphoryl)-acetate (5). Methyl phosphorylglycinate 4 (876 mg, 2.95 mmol) was dissolved in dioxane (3 mL) and cooled to 0° C. NaOH (1 N, 2.95 mL) was added dropwise over 15 min and the reaction was stirred until the starting material disappeared (~1 h) (TLC: $R_f$=0.5 1:1 pet. Ether/EtOAc, ninhydrin stain). The solution was acidified to ~pH 1 with 20% HCl and extracted with EtOAc (3×10 mL). The combined EtOAc extracts were washed with water (5 mL), brine (10 mL) and dried over $MgSO_4$. Concentration followed by recrystallization (EtOAc/pet. Ether) yield 616 mg (74%) of a white solid. Mp 155–156° C. ¹H NMR (CDCl₃): δ 9.21 (br s, 2 H), 5.57 (d, 1 H, J=9 Hz), 4.94 (dd, 1 H, J=9.0, 22.6 Hz), 3.88 (d, 3 H, J=11.1 Hz), 3.84 (d, 3 H, 11.6 Hz), 1.45 (s, 9 H). ¹³C NMR (CDCl₃): δ 168.05, 155.45, 81.41, 55.17(d, $J_{COP}$=7.6 Hz), 55.07 (d, $J_{COP}$=7.6 Hz), 52.12 (d, $J_{CP}$=150.4 Hz) 26.69. The acid (2.25 g, 7.94 mmol) and trimethylsilylethanol (1.42 mL, 9.93 mmol) were dissolved in $CH_2Cl_2$ (30 mL) and cooled to 0° C. DCC (1.80 g, 8.74 mmol) was added and the reaction was stirred for 8 h. The urea by-product was removed by filtration and the solution was concentrated. The residue was taken up in EtOAc (60 mL), washed with citric acid (2×10 mL), NaHCO$_3$ (2×10 mL), water (10 mL), brine (20 mL) and dried over MgSO$_4$. Concentration followed by chromatography (6:4 pet. Ether/EtOAc) gave 3.01 g (98%) of the TMSE ester 5 as a colorless oil that slowly solidified at −20° C. $^1$H NMR (CDCl$_3$): δ 5.31 (br d, 1 H, J =8.4 Hz), 4.81 (dd, 1 H, J=9.4, 22.1 Hz), 4.28 (m, 2 H), 3.82 (d, 3 H, J=3.1 Hz), 3.78 (d, 3 H, J=3.1 Hz), 1.43 (s, 9 H), 1.05 (m, 2 H), 0.03 (s, 9 H). $^{13}$C NMR (CDCl$_3$): δ 166.98, 148.44, 89.49, 64.94, 53.88 (d, J$_{COP}$=5.5 Hz), 51.96 (d, J$_{CP}$=147.1 Hz), 28.18, 17.36, −1.63.

Methyl (Z)-2-(benzyloxycarbonylamino)-3-(3-formylphenyl)-2-propenoate (6).

Phosphorylglycinate 3 (4.00 g, 12.1 mmol) was dissolved in 150 mL CH$_2$Cl$_2$ and tetramethylguanidine (1.67 mL, 13.3 mmol) was added. The reaction was stirred for 30 min, then isophthalaldehyde (16.20 g, 120.8 mmol) was added. The reaction was judged to be complete after 10 min by monitoring the disappearance of 3 by TLC (R$_f$=0.3, 1:1 pet. Ether/EtOAc, UV, veratraldehyde stain). The solution was diluted with 50 mL CH$_2$Cl$_2$ and washed with 10% citric acid (2×30 mL), NaHCO$_3$ (30 mL), water (30 mL), brine (80 mL) and then dried over MgSO$_4$. Concentration followed by chromatography (90:10 pet. Ether/EtOAc—excess isophthalaldehyde; 85:15 pet. Ether/EtOAc—product) gave 3.87 g (94%) of 6 as a thick colorless oil which solidified after several days at 4° C. m.p.=77–83° C. $^1$H NMR (CDCl$_3$): δ 9.89 (s, 1 H), 7.94 (s, 1 H), 7.80 (d, 1 H, J=7.7 Hz), 7.72 (d, 1 H, J=7.7 Hz), 7.47 (t, 1 H, J=7.7 Hz), 7.37 (s, 1 H), 7.32 (br s, 5 H), 6.67 (s, 1 H), 5.08 (s, 2 H), 3.84 (s, 3 H). $^{13}$C NMR (CDCl$_3$): δ 191.71, 165.34, 153.28, 136.47, 135.69, 135.01, 134.92, 134.56, 130.88, 129.13, 128.50, 128.34, 128.27, 125.12, 67.60, 52.85. Anal. Calcd for C$_{19}$H$_{17}$NO$_5$: C, 67.25 H, 5.05; N, 4.13. Found: C, 67.05; H, 5.18; N, 4.04.

Methyl (Z)-2-(benzyloxycarbonylamino)-3-(3-((Z)-2-(tert-butoxycarbonylamino)-3-(2-trimethylsilyl)ethoxy-3-oxo-1-propenyl)phenyl)-2-propenoate (7). Phosphorylglycinate 5 (2.80 g, 7.30 mmol) was dissolved in 10 mL of CH$_2$Cl$_2$, tetramethylguanidine (1.25 mL, 9.96 immol) was added, and the mixture was stirred for 30 min at rt. Aldehyde 6 (2.40 g, 7.08 mmol), dissolved in 10 mL CH$_2$Cl$_2$, was then added and the reaction was stirred for 24 h. The solution was diluted to 50 mL with CH$_2$Cl$_2$ and washed with 10% citric acid (2×10 mL), NaHCO$_3$ (10 mL), water (10 mL), brine (10 mL) and then dried over MgSO$_4$. Concentration followed by chromatography (9:1 pet. ether/EtOAc) gave 3.50 g (83%) of 7 as a colorless oil. $^1$H NMR (CDCl$_3$): δ 7.63 (s, 1 H), 7.47 (d, 2 H, J=6 Hz), 7.33–7.26 (m, 7 H), 7.18 (s, 1 H), 6.52 (br s, 1 H), 6.27 (br s, 1 H), 5.1 (s, 2 H), 4.34 (m, 2 H), 3.79 (s, 3 H), 1.37 (s, 9 H), 1.1 (m, 2 H), 0.08 (s, 9 H). $^{13}$C NMR (CDCl$_3$): δ 165.55, 165.42, 153.78, 152.51, 135.91, 134.81, 133.87, 131.02, 130.91, 130.29, 129.73, 128.64, 128.45, 128.18, 128.14, 126.87, 125.51, 124.84, 80.97, 67.48, 64.10, 52.58, 28.03, 17.42, −1.52. Anal. Calcd for C$_{31}$H$_{40}$N$_2$O$_8$Si: C, 62.39; H, 6.76; N, 4.69. Found: C, 62.14; H, 6.96; N, 4.60.

Methyl (S)-2-(benzyloxycarbonylamino)-3-(3-((S)-2-(tertbutoxycarbonylamino)-3-(2-trimethylsilyl)ethoxy-3-oxopropyl)phenyl)propanoate (8). The diacrylate 7 (1.50 g, 2.51 mmol) was dissolved in 8 mL of MeOH and degassed for 30 min with N. Rh(MeDUPHOS) catalyst was added (16 mg) and the reaction was subjected to 45–50 psi of H$_2$ on a Parr shaker for 12 h. The MeOH was evaporated. The residue was dissolved in CHCl$_3$ and passed through a layer of silica (7:3 pet. Ether/EtOAc) to give 1.45 g (96%) of a colorless oil. Diastereomeric ratios were determined to be 98:2 by $^1$H-NMR analysis (see Supporting Information). $^1$H NMR (CDCl$_3$): δ 7.33 (m, 5 H), 7.19 (t, 1 H, J=7.5 Hz), 7.00 (d, 1 H, J =11.4 Hz), 6.98 (d, 1 H, J =11.4 Hz), 6.88 (s, 1 H), 5.27 (br d, 1 H, J=7.9 Hz), 5.10 (s, 2 H), 4.98 (br d, 1 H, J=7.91 Hz), 4.63 (m, 1 H), 4.50 (m, 1 H), 4.17 (m, 2 H), 3.71 (s, 3 H), 3.07–2.96 (m, 4 H), 1.41 (s, 9 H), 0.95 (m, 2 H), 0.03 (s, 9 H). $^{13}$C NMR (CDCl$_3$): δ 172.36 (two peaks), 156.12, 155.58, 137.06, 136.80, 136.41, 130.99, 129.23, 129.01, 128.66, 128.61, 128.38, 127.45, 80.33, 67.46, 64.23, 55.32, 55.03, 52.82, 38.67 (two peaks), 28.79, 17.89, −1.03. Anal. Calcd for C$_{31}$H$_{44}$N$_2$O$_8$Si: C, 61.98; H, 7.38; N, 4.66. Found: C, 61.88; H, 7.38; N, 4.69.

3-(3-((S)-2-(benzyloxycarbonylamino)-3-methoxy-3-oxopropyl)phenyl)-(S)-2-(tertbutoxycarbonylamino) propanoic avid (9). TMSE ester 8 (1.00 g, 1.66 mmol) was dissolved in 15 mL of DMF and cooled to 0° C. Water (8 drops) was added to the solution. Bu$_4$N +F— (1.10 g, 3.49 mmol) was added and the reaction was stirred for 12 h, during which gas was evolved. The reaction was concentrated and the residue was dissolved in 40 mL EtOAc. HCl (0.5 N, 20 mL) was added to the organic layer and the layers were separated. The aqueous layer was extracted with EtOAc (3×10 mL) and the combined organic extracts were dried over MgSO$_4$. Concentration gave 802 mg (97%) of crude product which was used without purification for all subsequent transformations. $^1$H NMR (CDCl$_3$) δ 8.7–9.1 (br s, 1 H), 6.8–7.4 (m, 9 H), 6.06 (d, 0.5 H, J=8.4 Hz), 5.46 (d, 0.5 H, J=7.9 Hz), 5.0–5.3 (m, 3 H), 4.5–4.7 (m, 2 H), 3.70 (m, 3 H), 2.8–3.2 (m, 4 H), 1.4 (m, 9 H). $^{13}$C NMR (CDCl$_3$) a 174.74, 174.33, 172.51, 170.72, 157.40, 156.41, 155.76, 155.45, 136.91, 136.51, 136.04, 135.37, 131.65, 130.73, 129.21, 129.07, 128.84, 128.75, 128.61, 128.55, 128.06, 80.53, 80.29, 68.60, 68.43, 67.75, 55.62, 55.23, 54.77, 52.95, 38.88, 38.58, 38.49, 28.88, 26.09. Compound 9 appears to exist in two conformations in chloroform as indicated by the doubling of some resonances in the $^1$H and $^{13}$C spectra.

Methyl (S)-2-(benzyloxycarbonylamino)-3-(3-(S)-2-(tert-butoxycarbonylamino)-3-methoxy-3-oxopropyl)phenyl) propanoate (10). Crude acid 9 (119 mg, 0.238 mmol) was dissolved in 4.0 mL of CHCl$_3$:MeOH (3:1) and stirred. Trimethylsilyldiazomethane (2M in hexanes) was added dropwise until evolution of N$_2$ ceased and the solution maintained a yellow color. Concentration followed by chromatography (3:1 pet ether/EtOAc) yielded 101 mg (84%) of product as a colorless glass. [α]$^{25}$$_D$=+57.6°±0.8 (c=1.25 CHCl$_3$); $^1$H NMR (CDCl$_3$ δ 7.33 (s, 5 H), 7.19 (t, 1 H, J=7.5 Hz), 6.98 (m, 2 H), 6.86 (s, 1 H), 5.29 (d, 1 H, J=7.5 Hz), 5.09 (s, 2 H), 5.00 (d, 1 H, J=7.5 Hz), 4.64 (m, 1 H), 4.54 (m, 12 H), 3.71 (s, 3 H), 3.67 (s, 3 H), 3.04 (m, 4 H), 1.41 (s, 9 H); $^{13}$C NMR (CDCl$_3$) δ 172.74, 172.38, 156.15, 155.57, 136.88, 136.77, 136.51, 130.87, 129.29, 129.01, 128.64, 128.45, 80.46, 67.48, 55.32, 54.90, 52.83, 52.70, 38.67, 28.78. Anal. Calcd for C$_{27}$H$_{34}$N$_2$O$_8$: C, 63.02; H, 6.66; N, 5.44. Found: C, 60.42; H, 6.49; N, 5.13.

Methyl (S)-2-(tert-butoxycarbonylamino)-3-(3-((S)-2-(tert-butoxycarbonylamino)-3-methoxy-3-oxopropyl)henyl) propanoate (11). The ester 10 (94 mg, 0.18 mmol) was dissolved in MeOH (5 mL). Boc$_2$O (81 mg, 0.37 mmol) and 5% Pd/C (20 mg) was added, followed by H$_2$ addition via balloon while the reaction stirred for 10 h. In reactions where the reprotection of the amine was slow, another equivalent of Boc$_2$O was added along with a catalytic amount of DMAP (5%). When judged to be complete by TLC (disappearance of free amine, R$_f$=0.1, 7:3 pet ether/EtOAc, ninhydrin stain) the reaction was filtered, the solvent was evaporated, and the residue was chromatographed (excess Boc$_2$O-9:1 pet ether/EtOAc; product-7:3 pet. Ether/EtOAc) to give 88 mg (100%) of a colorless glass. $[\alpha]^{25}{}_D$=+46.30±0.5 (c=2.2 CHCl$_3$); $^1$H NMR (CDCl$_3$): δ 7.19 (t, 1 H, J=7.3 Hz), 6.98 (d, 2 H, J=7.9 Hz), 6.86 (s, 1 H), 5.01 (d, 2 H, J=7.3 Hz), 4.53 (m, 2 H), 3.68 (s, 6 H), 3.02 (m, 4 H), 1.39 (s, 18 H). $^{13}$C NMR: (CDCl$_3$) δ 172.15, 154.97, 136.19, 130.37, 128.66, 127.83, 79.85, 54.36, 52.10, 38.11, 28.19. Anal. Calcd for C$_{24}$H$_{36}$N$_2$O$_8$: C, 59.98; H, 7.55; N, 5.83. Found: C, 59.83; H, 7.52; N, 5.75.

α-Methyl (N-tert-butoxycarbonyl)-aspartate. The amino ester 11 (131 mg, 0.273 mmol) was dissolved in a mixture of CH$_3$CN (8 mL), CCl$_4$ (8 mL) and water (14 mL). RuO$_2$ (12 mg, 0.090 mmol) was added and the mixture was stirred vigorously. NaIO$_4$ (2.00 g, 9.35 mmol) was added in 3 portions over the course of 4 h, each time causing a gas emission and solution color change from black/gray to yellow. Additional NaIO$_4$ was added in three 300 mg portions until all starting material had disappeared by TLC (Rf=0.4, 7:3 pet. ether/EtOAc, ninhydrin stain). The mixture was diluted with 10 mL CH$_3$CN and 10 mL CHCl$_3$ and filtered. iPrOH was added to reduce the RuO$_4$, during which the solution turned from yellow to black, and the mixture was filtered and concentrated. The residue was taken up in 10 mL saturated NaHCO$_3$ and extracted with CH$_2$Cl$_2$ (2×4 mL). The water layer was acidified to ~pH 1 with 2 N HCl and extracted with CH$_2$Cl$_2$ (5×4 mL). The organic extracts were washed with water (5 mL), brine (10 mL) and dried (MgSO$_4$). Concentration of the solution left 48 mg (36%) of a colorless oil that slowly solidified at 4° C. mp 81–87° C., lit. mp 84–88° C.,$^{38}$89° C.$^{39}$ $[\alpha]°_D$=−17.9°±0.5 (c=1.45 MeOH); lit. $[\alpha]^{22}{}_D$=−17.8°(c=1 MeOH),$^{38}$ $[\alpha]^{23}{}_D$=−19.0° (c=1 MeOH).$^{39}$ $^1$H NMR (CDCl$_3$) δ 8.81 (br s, 1 H), 5.54 (d, 1 H, J=8 Hz), 4.58 (m, 1 H), 3.75 (s, 3 H), 3.04 (dd, 1 H, 3.8, J=17.2 Hz), 2.85 (dd, 1 H, 4.3, J=17.2 Hz), 1.44 (s, 9 H); $^{13}$C NMR: (CDCl$_3$) δ 175.85, 171.50, 155.50, 80.38, 52.75, 49.71, 36.62, 28.23.

Methyl (S)-2-(benzyloxycarbonylamino)-3-(3-(3-((2-(benzyloxy)-2-oxoethyl)amino)-(S)2-(tert-butoxycarbonylamino)-3-oxopropyl)phenyl)propanoate (12). Crude acid 9 (515 mg, 1.03 mmol) was dissolved in DMF (12 mL) along with HOBT (192 mg, 1.421 mmol), triethylamine (190 μL, 1.37 mmol), and glycine benzyl ester hydrotosylate (462 mg, 1.25 mmol). The reaction was cooled to 0° C. and DCC (249 mg, 1.20 mmol) was added. The reaction was allowed to warm to rt and was stirred for 24 h. The solution was diluted with 50 mL of EtOAc and cooled to 0° C. to precipitate salts. The solution was filtered through a bed of Celite, and then extracted with 10% citric acid (2×10 mL), saturated NaHCq (2×10 mL), water (5×5 mL), and brine (25 mL). Concentration of the solution followed by column chromatography (65:35 pet. Ether/EtOAc) gave the 567 mg (85%) of the coupled product 12 as a colorless glass. $^1$H NMR (CDCl$_3$): δ 7.26–7.32 (m, 10 H), 7.16 (t, 1 H, J=7.5 Hz), 7.06 (d, 1 H, J=7.9 Hz), 7.04 (s, 1 H), 6.95 (d, 1 H, J=7.5 Hz), 6.46 (br s, 1 H), 5.54 (d, 1 H, J=8.4 Hz), 5.21 (br s, 1 H), 5.12 (s, 2 H), 5.08 (br m, 1 H), 5.01 (s, 2 H), 4.63 (m, 1 H), 3.90 (br d, 2 H, J=4.9 Hz), 3.73 (s, 3 H), 2.93–3.17 (m, 4 H), 1.40 (s, 9 H). $^{13}$C NMR (CDCl$_3$): δ 172.39, 172.02, 169.95, 156.13, 155.76, 137.46, 136.81, 136.65, 135.64, 130.76, 129.16, 129.03, 128.92, 128.81, 128.61, 128.49, 128.32, 80.52, 67.52, 67.28, 56.16, 55.48, 52.81, 41.67, 39.00, 38.68, 28.70. Anal. Calcd for C$_{35}$H$_{41}$N$_3$O$_9$: C, 64.90; H, 6.38; N, 6.49. Found: C, 65.01; H, 6.39; N, 6.35.

Methyl (S)-9-(tert-butoxycarbonylamino)-5,8-dioxo-(S)-4,7-diazabicyclo[9.3.1]pentadeca-1(15), 11,13-triene-3-carboxylate (13). The fully protected dipeptide 12 (1.61 g, 2.49 mmol) was dissolved in MeOH (40 mL) and 5% Pd/C (300 mg) was added. H$_2$ was added via balloon and the reaction was stirred vigorously for 12 h. TLC analysis showed the disappearance of starting material (Rf=0.5, 50:50 pet. ether/EtOAc, ninhydrin stain). The catalyst was removed by filtration and the solution was concentrated. Redissolving the semi-solid in MeOH followed by addition of EtOAc and evaporation gave 1.00 g (95%) of a hygroscopic granular white solid. Proton NMR showed the absence of benzylic groups. $^1$H NMR (CDCl$_3$) (peaks broad due to zwitterion): δ 7.9 (br s, 3 H), 6.8–7.2 (m, 5 H), 5.4 (br s, 1 H), 4.4 (br s, 1 H), 4.0 (br s, 1 H), 3.62 (s, 3 H), 3.58 (br s, 2 H), 2.7–3.2 (m, 4 H), 1.23 (s, 9 H), $^{13}$C NMR (CDCl$_3$): δ 174.21, 172.32, 155.94, 138.90, 137.26, 131.05, 128.77, 128.45, 127.90, 78.89, 56.33, 55.69, 52.52, 42.51, 25.38, 28.95. Anal. Calcd for C$_{20}$H$_{29}$N$_3$O$_7$·H$_2$O: C, 54.41; H, 7.08; N, 9.52. Found: C, 54.52; H, 7.15; N, 8.94. The amino acid (1.00 g, 2.36 mmol) was dissolved in DMF (1.25 L) and cooled to 0° C. DPPA (709 μL, 2.83 mmol) was added, followed by DIEA (1.03 mL, 5.90 mmol). The reaction was stirred under N$_2$ for 7 d at 4° C. The solvent was removed in vacuo, dissolved in minimal CHCl, and chromatographed (120:2:1 CHCl$_3$/MeOH/AcOH), to give 800 mg (80%) of a white solid. mp 245° C. (dec); $^1$H NMR (CDCl$_3$/DMSO-d$_6$): δ 7.95 (t, 1 H, J=6.4 Hz), 7.12 (d, 1 H, J=8.8 Hz), 7.06 (t, 1 H, J=7.5 Hz), 6.90 (d, 1 H, J=7.5 Hz), 6.82 (d, 1 H, J=7.5 Hz), 6.60 (s, 1 H), 5.98 (d, 1 H, J=7.9 Hz), 4.52 (m, 1 H), 4.11 (m, 1 H), 3.72 (dd, 1 H, J=6.8, 14.1 Hz), 3.61 (s, 3 H), 3.40 (dd, 1 H, J=6.2, 14.1 Hz), 3.01 (dd, 1 H, J=3.1, 13.8 Hz), 2.86 (d, 2 H, J=6.7 Hz), 2.60 (dd, 1 H, J=7.5 Hz, 12.7 Hz), 2.31 (dd, 1 H, J=5.7, 13.2 Hz), 1.30 (s, 9 H). $^{13}$C NMR (CDCl$_3$): δ 172.07 (two peaks), 169.27, 155.45, 136.98, 136.40, 133.26, 129.31, 128.69, 127.83, 79.41, 56.57, 53.01, 52.49, 44.00, 39.06, 37.05, 29.11. Anal. Calcd for C$_{20}$H$_{27}$N$_3$O$_6$: C, 59.25,; H, 6.71; N, 10.36. Found: C, 59.15; H, 6.76; N, 10.29.

(S)-9-(tert-butoxycarbonylamino)-5,8-dioxo-(S)-4,7-diazabicyclo[9.3.1]pentadeca1-(15),11,13-triene-3-carboxylic acid (1b). Cyclic peptide ester 13 (190 mg, 0.45 mmol) was dissolved in warm THF/MeOH (40 mL) and cooled to rt. NaOH (1 N, 0.5 mL) was slowly added with stirring. After 1 h, the completed reaction (TLC-disappearance of 13, 120:2:1 CHCl$_3$/MeOH/AcOH, ninhydrin stain) was concentrated and the residue was dissolved in water. Dropwise addition of 2 N HCl induced precipitation of the product which was collected on a filter and dried under vacuum in a dessicator to give a white solid (140 mg, 74%). mp >250° C; $^1$H NMR (CDCl$_3$/DMSO-d$_6$): δ 8.30 (br s, 1 H), 7.98 (t, 1 H, J=6.3 Hz), 7.23 (d, 1 H, J=9.4 Hz), 7.14 (t, 1 H, J=7.0 Hz), 6.96 (d, 1 H, J=7.0 Hz), 6.66 (s, 1 H), 6.37 (d, 1 H, J=7.8 Hz), 4.39 (m, 1 H), 4.05 (m, 1 H), 3.85 (dd, 1 H, J=8.8, 14.0 Hz), 3.27 (1 H, obscured by H$_2$O peak), 3.02–2.78 (m, 3 H), 2.67 (dd, 1 H, 8.2 Hz, J=12.9 Hz), 1.34 (s, 9 H); $^{13}$C NMR (DMSO-d$_6$; CD$_3$OD): δ 173.27, 173.05, 169.97, 156.14, 137.34, 136.43, 133.51, 129.55, 128.80, 128.18, 80.24, 56.76, 52.70, 49.45, 44.16, 37.58, 28.73. Anal. Calcd for C$_{19}$H$_{25}$N$_3$O$_6$·H$_2$O: C, 55.74; H, 6.65; N, 10.26. Found: C, 55.16; H, 6.59; N, 9.90.

References (1) Richardson, J. S. *Adv. Protein Chem.* 1981, 34, 167–339.
(2) Ptashne, M. A. *Genetic Switch;* 2$^{nd}$ ed.; Cell Press & Blackwell Scientific Publications: Cambridge, Mass., 1992.
(3) Mondragón, A.; Harrison, S. C. *J. Mol. Biol.* 1991, 219, 321–334.
(4) Klemm, J. D.; Rould, M. A.; Aurora, R.; Herr, W.; Pabo, C. O. *Cell* 1994, 77, 21–32.

(5) Ruvkun, G.; Finney, M. *Cell* 1991, 64, 475–478.
(6) Schneider, J. P.; Kelly, J. W. *Chem. Rev.* 1995, 95, 2169–2187.
(7) Mullen, d. G.; Barlett, P. A. Pept. 1990, *Proc. Eur. Pept. Symp.*, 21$^{st}$ 1991, 364–365.
(8) Diaz, H.; Tsang, K. Y.; Choo, D.; Kelly, J. W. *Tetrahedron* 1993, 49, 3533–45.
(9) Tsang, K. Y.; Diaz, H.; Graciani, N.; Kelly, J. W. *J. Am. Chem. Soc.* 1994, 116, 3988–4005.
(10) Schneider, J. P.; Kelly, J. W. *J. Am. Chem. Soc.* 1995, 117, 2533–2546.
(11) Struthers, M. D.; Cheng, R. P.; Imperiali, B. *Science* 1996, 271, 342–348.
(12) Duthaler, R. O. *Tetrahedron* 1994, 50, 1539–1650.
(13) Ovchinnikov, Y. A.; Ivanov, V. T. *Tetrahedron* 1975, 31, 2177–2209.
(14) Manesis, N. J.; Goodman, M. *J. Org. Chem.* 1987, 52, 5331–5341.
(15) Osapay, G.; Taylor, J. W. *J. Am. Chem. Soc.* 1990, 112, 6046–6051.
(16) Sugg, E. E.; Castrucci, A. M. d.; Hadley, M. E.; van Binst, G.; Hruby, V. *Biochemistry* 1988, 27, 8181–8188.
(17) Creighton, T. E. *Methods Enzymol.* 1984, 107, 305–329.
(18) Miller, S. J.; Grubbs, R. H. *J. Am. Chem. Soc.* 1995, 117, 5855–5856.
(19) Stachel, S. J.; Habeeb, R. L.; Van Vranken, D. L. *J. Am. Chem. Soc. 1996, 118, 1225–1226.*
(20) Mark, L.; Ungvari, F. *J. Organomet. Chem.* 1992, 432, 1–214.
(21) Kagan, H. B.; Sasaki, M. *Optically Active Phosphines: Preparation, Uses, and Chiroptical Properties*; J. Wiley & Sons: N.Y., 1990; Vol. 1.
(22) Williams, R. M. *Synthesis of Optically Active α-Amino Acids*; Pergamon Press: Oxford, 1989; Vol. 7.
(23) Burk, M. J.; Feaster, J. E.; Nugent, W. A.; Harlow, R. L. *J. Am. Chem. Soc.* 1993, 115, 10125–10138.
(24) Burk, M. J.; Lee, J. R.; Martinez, J. P. *J. Am. Chem. Soc.* 1994, 116, 10847–10848.
(25) Burk, M. J.; Gross, M. F.; Martinez, J. P. *J. Am. Chem. Soc.* 1995, 117, 9375–9376.
(26) Schmidt, U.; Lieberknect, A.; Wild, J. *Synthesis Communications* 1984, 53–60.
(27) Maryanoff, B. E.; Reitz, A. B. *Chem Rev.* 1989, 89, 863–927.
(28) Schmidt, U.; Meyer, R.; Leitenberger, V.; Griesser, H.; Lieberknecht, A. *Synthesis* 1992, 1025–1030.
(29) Bartlett, P. A.; Shea, G. T.; Telfer, S. J.; Waterman, S. In *Molecular Recognition: Chemical and Biological Problems*; Roberts, S. M., Ed.; Royal Society of Chemistry: London, 1989, p 182–96.
(30) Etzkorn, F. A.; Guo, T.; Lipton, M.; Goldberg, S.; Bartlett, P. A. *J. Am. Chem. Soc.* 1994, 116, 10412–10425.
(31) Bartlett, P. A.; Etzkorn, F. A.; Guo, T.; Lauri, G.; Liu, K.; Lipton, M.; Morgan, B. P.; Shea, G. T.; Shrader, W. D.; Waterman, S. *Proceedings of the Robert A. Welch Conference on Chemical Research* 1991, XXXV, 45–68.
(32) Schmidt, U.; Griesser, H.; Leitenberger, V.; Lieberknecht, A.; Mangold, R.; Meyer, R.; Riedl, B. *Synthesis* 1992, 487–490.
(33) Efficient synthesis of the cyclization precursor 12, Scheme 5, could conceivably have been achieved by reaction of a dipeptide phosphonate with the mono-aldehyde 6, followed by hydrogenation. The Horner-Wittig reaction of dipeptide synthons having the phosphonate in the C-terminal position such as methyl Boc-(S)-Ile-2-(dimethoxyphosphoryl)acetate with aryl aldehydes has been reported.[25] However, in our sterically-congested target, the reaction of benzyl 2-(Cbz)amino-2-(dimethoxyphosphoryl) acetyl-glycinate with 6 gave a very poor yield in the second Horner-Wittig reaction. Inverting the order by reacting the dipeptide phosphonate in the first step and 3 in the second step did not improve the yield. We concluded that stepwise synthesis of the tripeptide backbone was necessary, and suitable for cassette synthesis with amino acids other than Gly.

(34) The activity of the catalyst from Strem varied from batch to batch and the turnover ratio did not approach that reported in the literature. In our experience, rigorously oxygen-free conditions are required to attain total conversion to product. In this initial work, Rh(MEDUPHOS) was used, by Rh(EtDUPHOS) gives slightly better enantioselectivity.

(35) The recycle delay was increased to 10 sec and no line-broadening was used in processing to minimize integration errors due to the long relaxation times for aromatic protons. The spectra were acquired at 500 MHz for enhanced resolution.

(36) Tanaka, K.-i.; Yoshifuji, S.; Nitta, Y. *Chem. Pharm. Bull.* 1988, 36, 3125–3129.
(37) Schuda, P. F.; Cichowicz, M. b.; Heimann, M. R. *Tetrahedron Lett.* 1983, 24, 3829–3830.
(38) Tohdo, K.; Hamada, Y.; Shiori, T. *Synlett* 1994, 105–106.
(39) Cantacuzene, D.; Guerreiro, C. *Tetrahedron* 1989, 45, 741–748.
(40) NMR samples at normal concentrations in $CDCl_3$ were found to form gels upon standing for a few hours. The target ester 13 was soluble only DMF, DMSO, or mixtures of THF/MeOH, $CHCl_3$/DMSO. Boc-protected intermediates 8 and 13 were found to decompose upon standing in $DCCl_3$ due to the presence of DCl.
(41) Shiori, T.; Ninomiya, K.; Yamada, S. *J. Am. Chem. Soc.* 1972, 94, 6203–5.
(42) Zoller, U.; Ben-Ishai, D. *Tetrahedron* 1975, 31, 863–866.

Supporting Information 2-(Benzyloxycarbonylamino)-2-hydroxyacetic acid. Prepared by the method of Zoller et al.[42] mp 194–197° C. (lit. 196–198° C.);[42] $^1$H NMR (DMSO-$d_6$): δ 12.74 (br s, 1 H), 8.07 (d, 1 H, J=8.2 Hz), 7.31 (m, 5 H), 6.18 (br s, 1 H), 5.16 (d, 1 H, J=8.8 Hz), 5.00 (s, 2 H). $^{13}$C NMR (DMSO-$d_6$): δ 171.97, 156.42, 137.79, 129.29, 128.75, 74.11, 66.44.

Methyl 2-(benzyloxycarbonylamino)-2-methoxyacetate. Prepared by the method of Zoller et al.[42] mp 74–75° C. (lit. 76–78° C.).;33 $^1$H NMR ($CDCl_3$): δ 7.4 (s, 5 H), 5.95 (d, 1 H, J=7.5 Hz), 5.35 (d, 1 H, J=9.1 Hz), 5.15 (s, 2 H), 3.79 (s, 3 H), 3.45 (s, 3 H). $^{13}$C NMR ($CDCl_3$): δ 168.51, 156.20, 136.30, 129.10, 128.88, 128.69, 81.18, 67.93, 56.75, 53.40.

Methyl 2-(benzyloxycarbonylamino)-2-(dimethoxyphosphoryl)acetate (3). Prepared by the method of Schmidt et al.[26] mp 80° C. (lit. 80° C.);[26] $^1$H NMR ($CDCl_3$): δ 7.35 (br s, 5 H), 5.63 (d, 1 H, J=6.8 Hz), 5.13 (s, 2 H), 4.92 (dd, 1 H, J=9.0, 22.2 Hz), 3.82 (s, 3 H), 3.80 (s, 3 H), 3.76 (s, 3 H). $^{13}$C NMR ($CDCl_3$): δ 167.11, 155.47, 135.76, 128.45, 128.24, 128.05, 67.54, 54.06 (d, $J_{COP}$=6.5 Hz), 53.92 (d, $J_{COP}$=6.5 Hz), 53.12 (d, $J_{CP}$=148.2 Hz).

Methyl 2-(tert-btoxycarbonylamino)-2-(dimethoxyphosphoryl)-acetate (4). Prepared by the method of Schmidt et al.[26] The oil was chromatographed (50:50 pet. Ether/EtOAc) to give 1.7 g (94%) of 4 as a colorless glass. $^1$H NMR (CDCl$_3$): δ 5.34 (d, 1 H, J=7.7 Hz), 4.85 (dd, 1 H, 9.0, J=22.2 Hz), 3.82 (d, 3 H, J=3 Hz), 3.81 (s, 3 H), 3.79 (d, 3 H, J=2.6 Hz), 1.43 (s, 9 H). $^{13}$C NMR (CDCl$_3$): δ 167.97, 155.31, 81.43, 54.56 (d, J$_{COP}$=5.5 Hz), 54.48 (d, J$_{COP}$=5.5 Hz), 53.74, 52.15 (d, J$_{CP}$=148.2 Hz), 28.67.

---

---

What is claimed is:

1. A compound of the formula

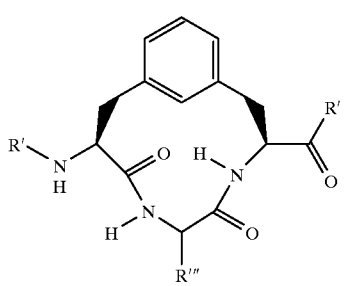

wherein R' and R" are independently the same or different protective groups, and R'" can be any amino acid side chain.

2. A compound of the formula

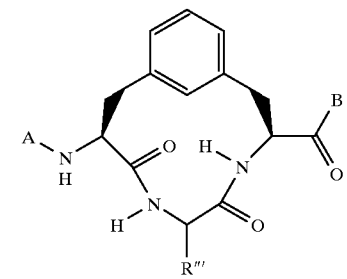

wherein A and B are independently peptide helices and R'" is any amino acid side chain.

3. The compound of claim 2, wherein both A and B have a helix configurations.

4. The compound of claim 3, wherein A and B are the helical peptides of a DNA binding domain selected from the group consisting of a regulator bacteriophage protein and a regulator eukaryotic homeodomain protein.

5. The compound of claim 4, wherein said bacteriophage regulator protein is repressor protein or Cro and said eukaryotic homeodomain protein is Oct-1.

* * * * *

UNITED STATES PATENT AND TRADEMARK OFFICE
CERTIFICATE OF CORRECTION

PATENT NO.     : 6,080,838  
DATED          : June 27, 2000  
INVENTOR(S)    : Felicia A. Etzkorn et al.

It is certified that error appears in the above-identified patent and that said Letters Patent is hereby corrected as shown below:

<u>Column 1,</u>
The following paragraph is inserted immediately after the title:

-- U.S. Government Rights
This invention was made with United States Government support under Grant No. GM52516, awarded by the National Institutes of Health. The United States Government has certain rights in the invention. --

Signed and Sealed this

Eleventh Day of June, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,080,838 |
| APPLICATION NO. | : 08/978023 |
| DATED | : June 27, 2000 |
| INVENTOR(S) | : Felicia A. Etzkorn et al. |

It is certified that error appears in the above-identified patent and that said Letters Patent is hereby corrected as shown below:

At Column 1, Line 3-4, the following paragraph is inserted immediately after the title:

U.S. Govenment Rights

This invention was made with United States Government support under Grant No. GM37537, awarded by the National Institutes of Health. The United States Government has certain rights in the invention.

Signed and Sealed this

Twenty-first Day of August, 2007

JON W. DUDAS
*Director of the United States Patent and Trademark Office*